United States Patent
Brands

(12) 
(10) Patent No.: US 6,313,364 B1
(45) Date of Patent: Nov. 6, 2001

(54) SYNTHESIS OF CYCLOPROPANEACETYLENE USING A CATALYTIC DECARBOXYLATION REACTION

(75) Inventor: Karel M. J. Brands, Jersey City, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/698,827

(22) Filed: Oct. 27, 2000

Related U.S. Application Data

(60) Provisional application No. 60/161,958, filed on Oct. 28, 1999.

(51) Int. Cl.[7] .............................. C07C 2/00; C07C 4/04; C07C 5/32
(52) U.S. Cl. .......................... 585/534; 562/506
(58) Field of Search ............................ 585/534; 562/506

(56) References Cited

U.S. PATENT DOCUMENTS

| | | |
|---|---|---|
| 5,519,021 | 5/1996 | Young et al. . |
| 5,663,467 * | 9/1997 | Thompson et al. . |
| 5,856,492 | 1/1999 | Chen et al. . |
| 5,922,864 | 7/1999 | Frey et al. . |
| 6,028,237 * | 2/2000 | Parsons et al. . |

FOREIGN PATENT DOCUMENTS

| | | |
|---|---|---|
| WO 95/20389 | 8/1995 | (WO) . |
| WO 96/37457 | 11/1996 | (WO) . |
| WO 99/06341 | 2/1997 | (WO) . |
| WO 98/30543 | 7/1998 | (WO) . |

OTHER PUBLICATIONS

C. Hudson, et al., "A Quantitative Analysis of Cyclopropyl Beta Hyperfine Splittings", Journal of the American Chemical Society, vol. 94:4, pp. 1158–1163, (Feb. 23, 1972).

H. Miltzer, et al., "Versatile Syntheses of Alkynyl–and Substituted Alkynylcyclopropanes: 2–Alkoxyethynylcyclopropanes for the Anellation of Bicyclo[3.3.0]octane Fragments", Synthesis, pp. 998–1012, (1993).

A. Thompson et al., "Use of an Ephedrine Alkoxide to Mediate Enantioselective Addition of an Acetylide to a Prochiral Ketone: Asymmetric Synthesis of the Reverse Transcriptase Inhibitor L–743, 726", Tetrahedron Letters, vol. 36, No. 49, pp. 8937–8940, (1995).

J. Salaun, "Preparation and Substituent Effect in the Solvolysis of 1–Ethynylcyclopropyl Tosylates", J. Org. Chem., vol. 41, No. 7, pp. 1237–1240, (1976).

F. Carey et al., "Silicon–Containing Carbanions. II. Ketene Thioacetal Synthesis via 2–Lithio–2–trimethylsilyl–1, 3–dithiane", J. Org. Chem., vol. 37, No. 12, pp. 1926–1929, (1972).

H. Takeshita et al., "Sensitized Photoreduction of Dioxetanes to cis–1,2–Glycols: Solvent and Sensitizer Dependencies on the Singlet Oxygen Oxidation", J. Org. Chem., vol. 43, No. 15, pp. 3080–3083 (1978).

D. J. Peterson, "A Carbonyl Olefination Reaction Using Silyl–Substituted Organometallic Compounds", J. Org. Chem., vol. 33, No. 2, pp. 780–784 (1968).

Chemical Abstracts No. 78:124091, abstract of W. Schoberth et al., "Eine Einfache Herstellungsmethode fur Cyclopropylacetylen", Synthesis, p. 703, (1972).

L. A. Akopyan et al., "Catalytic Decarboxylation of Alpha–Acetylenic Acids", J. of General Chemistry, vol. 44, No. 8, Part 2, p. 1804 (1974).

* cited by examiner

Primary Examiner—Gary Geist
Assistant Examiner—Hector M Reyes
(74) Attorney, Agent, or Firm—Valerie J. Camara; Kenneth R. Walton; Melvin Winokur

(57) ABSTRACT

The present invention relates to a process for the preparation of cyclopropaneacetylene by the two step process: (1) an alkylation of propiolic acid with a 1,3-disubstituted propane followed by a cycloalkylation to give a 3-cyclopropaneacetylene carboxylic acid; and (2) decarboxylation of 3-cyclopropaneacetylene carboxylic acid in the presence of copper catalyst.

21 Claims, No Drawings

SYNTHESIS OF CYCLOPROPANEACETYLENE USING A CATALYTIC DECARBOXYLATION REACTION

This application claims benefit of U.S. Provisional Application No. 60/161,958 filed Oct. 28, 1999.

FIELD OF THE INVENTION

The present invention relates to a process for the preparation of cyclopropaneacetylene (CPA) by a catalytic decarboxylation reaction.

BACKGROUND OF THE INVENTION

A retrovirus designated human immunodeficiency virus (HIV) is the etiological agent of the complex disease that includes progressive destruction of the immune system (acquired immune deficiency syndrome, AIDS) and degeneration of the central and peripheral nervous system. A common feature of retrovirus replications is reverse transcriptase to generate DNA copies of HIV sequences, a required step in viral replication. It is known that some compounds are reverse transcriptase inhibitors and are effective agents in the treatment of AIDS and similar diseases, e.g., azidothylmidine or AZT. Cyclopropaneacetylene (CPA) is a key raw material for the preparation of an inhibitor of HIV reverse transcriptase, which is known as DMP-266 having a chemical name of (−)6-chloro-4-cyclopropylenthynyl-4-trifluoromethyl-1,4-dihydro-2H-3,1-benzoxanzin-2-one.

The synthesis of DMP-266 and structurally similar reverse transcriptase inhibitors are disclosed in U.S. Pat. No. 5,519,021, and the corresponding PCT International Patent Application WO 95/20389, which published on Aug. 3, 1995. Additionally, the asymmetric synthesis of an enantiomeric benzoxazinone by a highly enantioselective acetylide addition and cyclization sequence has been described by Thompson, et. al., Tetrahedron Letters 1995, 36, 8937–8940, as well as the PCT publication, WO 96/37457, which published on Nov. 28, 1996.

In addition, various aspects of the synthesis of DMP-266 have been disclosed in United States Patents. U.S. Pat. No. 5,663,467 discloses a synthesis of CPA involving cyclization of 5-halo-1-pentyne in base. U.S. Pat. No. 5,856,492 discloses a synthesis of a chiral mediator, and U.S. Pat. No. 5,922,864 discloses an efficient method to prepare DMP-266 by a cyclization reaction. A process for making chiral alcohol is published on Jul. 16, 1998 in PCT Publication No. WO 98/30543. Several methods have been described in the published literature for preparation of cyclopropaneacetylene. C. E. Hudson and N. L. Bauld, J. Am. Chem. Soc. 94:4, p. 1158 (1972); J. Salaun, J. Org. Chem. 41:7, p. 1237 (1976); and W. Schoberth and M. Hanack, Synthesis p. 703 (1972), disclose methods for the preparation of cyclopropylacetylene by dehydrohalogenating 1-cyclopropyl-1,1-dichloroethane. Miltzer, H. C. et al., Synthesis, 998 (1993) disclose a method for preparation of cyclopropylalkenes by halogenating an enolether, reacting the alkyl 1,2-dihaloether with propargyl magnesium bromide, and cyclizing to give a 2-alkoxy-1-ethynylcyclopropane. F. A. Carey and A. S. Court, J. Org. Chem., Vol. 37, No. 12, p. 1926 (1972) disclose the use of a modified Wittig-Homer olefin synthesis for organic transformations. D. J. Peterson, J. Org. Chem., Vol. 20C, No. 33, p. 780 (1968) describes the application of olefination to make vinyl sulfides and H. Takeshita and T. Hatsui, J. Org. Chem. Vol. 43, No. 15, p. 3083 (1978) disclose the use of potassium 3-aminopropylamide in base-catalyzed prototropic reactions.

However, the currently available ways to prepare CPA, for example synthesizing CPA from 5-chloro-1-pentyne, are not efficient in a large-scale production of CPA, and often have problems with impurities in the final product. As a result, there is a need for an alternative practical way to prepare CPA.

Therefore, it is an object of the present invention to provide a more efficient way to produce CPA, which involves a novel catalytic decarboxylation process.

SUMMARY OF THE INVENTION

The present invention relates to a process for the preparation of cyclopropaneacetylene (CPA) by a two step process. In the first step, alpha-acetylenic acid (propiolic acid) is cycloalkylated with a 3-carbon containing bis-electrophile yielding the crystalline cyclopropaneacetylene carboxylic acid. In the second step, the latter intermediate, cyclopropaneacetylene carboxylic acid, is decarboxylated in the presence of a copper catalyst to yield CPA.

A process for the preparation of cyclopropaneacetylene (CPA) comprises the steps of: (a) alkylating propiolic acid with a 1,3-disubstituted propane in a first base and an aprotic solvent to produce a reaction mixture containing a 6-substituted 2-hexynoic acid; (b) intramolecular cycloalkylation of the 6-substituted 2-hexynoic acid by addition of a second base to produce a reaction mixture containing cyclopropaneacetylene carboxylic acid; and (c) decarboxylating the cyclopropaneacetylene carboxylic acid with a copper catalyst in polar aprotic solvent to give a cyclopropaneacetylene (CPA).

DETAILED DESCRIPTION OF THE INVENTION

The present invention is directed to a process for the preparation of cyclopropaneacetylene (CPA) by a two-step process as shown below:

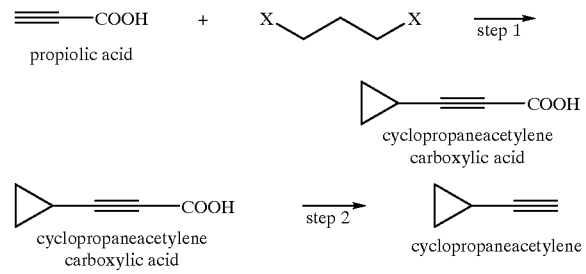

In the first step, about one equivalent of propiolic acid is mixed with at least one equivalent of the first base in aprotic solvents, preferably in a mixture of hexamethyl phosphoric triamide (HMPA) and THF, at a temperature between about −60° C. and about −80° C. The first base may be present in amounts between about 1.0 equivalent to about 3.0 equivalents relative to the amount of propiolic acid, preferably between about 2.0 and about 2.5 equivalents. Upon contact with the first base, the solution is allowed stand at temperature between about 0° C. to about −20° C., preferably at about −15° C., for time sufficient for the reaction to occur, generally from about 30 minutes to about an hour. After cooling the reaction mixture to about −50° C. to about −100° C., preferably about −70° C. to about −80° C., approximately one equivalent of 1,3-disubstituted propane, preferably 1-bromo-3-chloropropane, is added. The mixture is then allowed to stand at a temperature between about −10° C. and about −20° C. for about an hour before adding a second base to the reaction mixture, which is about one equivalent of a freshly prepared solution of lithium diisopropylamide (LDA). The resulting mixture is then allowed to stand at a temperature of between about −10° C. and about −20° C. for sufficient time to complete the reaction, generally from about an hour to about two hours. The reactions of above alkylation and cycloalkylation (step 1) occur at a temperature range of between about 0° C. and about −100° C. The mixture is then quenched with a sodium bicarbonate solution and washed with organic solvent, preferably diethyl ether. The pH of the aqueous layer is adjusted to about 1.0 with acid, preferably HCl, and then extracted with organic solvent, preferably diethylether. The combined extracts are dried and concentrated in usual fashion yielding crude cyclopropaneacetylene carboxylic acid. Pure cyclopropaneacetylene carboxylic acid can be obtained via crystallization from organic solvent, preferably from diethylether.

In the second step, the reaction is carried out in a polar aprotic solvent, preferably in dimethylformamide (DMF). In carrying out the reaction, cyclopropaneacetylene carboxylic acid produced in Step 1 is added to the solvent containing a catalytic amount of copper catalyst, preferably cuprous chloride. The mixture is then allowed to stand at a temperature of between about 50° C. and about 100° C. for a time sufficient to complete the reaction to form CPA, generally from about an hour to about two hours. After completion of the reaction, CPA is recovered from the reaction mixture by partitioning between water and organic solvent, preferably n-octane, to obtain the final compound CPA.

For the purpose of this invention, the aprotic solvent is selected from the group consisting of tetrahydrofuran (THF), 2,5-dimethyltetrahydrofuran, 1,4-dioxane, 1,3-dioxolane, methyl-tert-butyl ether (MTBE), diethoxymethane, dimethoxyethane, cyclohexane, pentane, hexane, toluene, hexamethyl phosphoric triamide (HMPA), dimethylpropyleneurea (DMPU) and mixtures of thereof. The preferred aprotic solvent is the mixture of THF and hexamethyl phosphoric triamide (HMPA). The term aprotic solvent means a type of solvent which neither donates nor accepts protons.

The first base used in the present invention is selected from the group consisting of sodium hydride, lithium hydride, potassium hydride, alkyl lithium, and alkyl potassium, such as n-butyl lithium, phenyl lithium, and butyl potassium. The term alkyl refers to lower alkyls such as methyl, ethyl, isopropyl, butyl, propyl and the like. The preferred first base is n-butyl lithium. The base may be used in amounts between about 1.0 equivalent to about 3.0 equivalents relative to the amount of propiolic acid, and preferably between about 2.0 and about 2.5 equivalents.

The 1,3-disubstituted propane used in this invention has a formula X-(CH$_2$)$_3$-X, wherein X represents the same or different substituents or mixtures thereof, which is selected from the group consisting of: Cl, Br, I, perfluoroalkyl sulfonates, alkyl sulfonates, and aryl sulfonates, such as CH$_3$SO$_3$- and CH$_3$PhSO$_3$-. The preferred substituted propane is 1-bromo-3-chloropropane.

The second base used in the present invention is a non-nucleophilic base, which is selected from the group consisting of lithium diisopropylamide (LDA), lithium bis(trimethylsilyl)amide, sodium bis(trimethylsilyl)amide, potassium bis(trimethylsilyl)amide, potassium tert-butoxide, sodium hydride, lithium hydride, and potassium hydride. The same base may be used as both the first base and the second base.

The non-nucleophilic base solution of lithium diisopropylamide (LDA) is prepared in situ by adding 10 mL of 2.5 M n-butyl lithium in hexane to a solution of 3.5 mL of diisopropylamine in 10 mL THF at about 0° C. Lithium bis(trimethylsilyl)amide is prepared in situ by adding n-butyl lithium in hexane to a solution of hexamethyldisilazane.

The polar aprotic solvent of the present invention is selected from the group consisting of dimethyl formamide (DMF), dimethylacetamide (DMA), acetonitrile, N-methylpyrrolidinone (NMP), and mixtures thereof. The preferred polar aprotic solvent is dimethyl formamide.

The copper catalysts used in the decarboxylation step (step 2) include copper powder (Cu) and salts such as CuX and CuX$_2$, wherein X is selected from the group consisting of Cl, Br, I, SO$_4$, CN, ClO$_4$, NO$_3$, acetylacetonate, CH$_3$CO$_2$, and CF$_3$SO$_2$. The preferred catalyst is CuCl.

CPA can be isolated, after aqueous quench of the reaction, by extraction into an organic solvent, such as hexane or toluene. Alternatively, CPA can be isolated and purified by a distillation directly from the reaction mixture.

The reagents used in the present invention are either commercially available or may be prepared by synthetic methods commonly known in the art.

The following examples are intended to illustrate the present invention but are not intended to limit the reasonable scope thereof.

EXAMPLE

Reaction Scheme

STEP 1

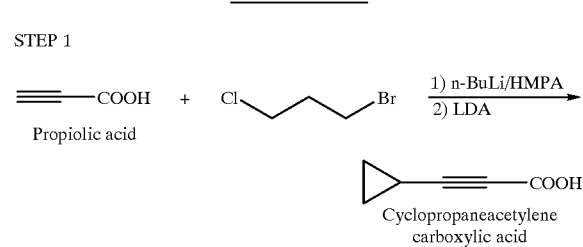

STEP 2

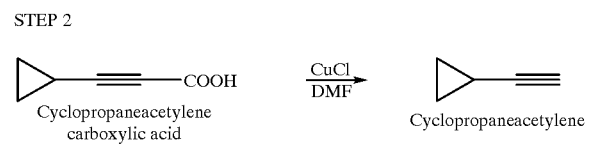

Procedure

Step 1: Preparation of Cyclopropaneacetylene Carboxylic Acid

A solution of propiolic acid (1.65 g; 23.1 mmol) in a mixture of dry THF(80 mL) and dry hexamethylphosphortriamide (HMPA; 20 mL) was cooled to about −70° C. A solution of n-BuLi in hexane (2.5 M; 20 mL; 50 mmol) was added slowly at such a rate that the temperature could be maintained at about <−65° C. The resulting slurry was allowed to warm to about −15° C. and aged for about 30 minutes. After cooling the mixture to about −70° C., 1-bromo-3-chloropropane (4.00 g 25.4 mmol) was added in one portion. The reaction was aged at about −15° C. for about an hour before a freshly prepared solution of LDA (prepared by adding 10 mL of 2.5 M n-BuLi in hexane to a solution of 3.5 mL of diisopropylamine in 10 mL of THF at about 0° C.) was added in one portion. The resulting mixture was aged for about an hour at about −15° C., quenched with sodium bicarbonate solution (100 mL) and washed with diethyl ether (100 mL). The pH of the aqueous layer was adjusted to about 1.0 with 10% HCl and extracted with diethyl ether (3×50 mL). The combined extracts were dried and concentrated in the usual fashion yielding crude cyclopropaneacetylene carboxylic acid (1.75 g assayed by $^1$H-NMR: 69% assay yield). Pure product could be obtained via crystallization from ether.

Step 2: Preparation of Cyclopropaneacetylene

A mixture of cyclopropaneacetylene carboxylic acid (1.00; 9.08mmol) and cuprous chloride (45 mg; 0.45 mmol) in DMF (10 mL) was heated at about 50° C. in a sealed tube. After about two hours, the tube was cooled in dry ice and its contents partitioned between water (10 mL) and n-octane (25 mL). The organic layer was washed with water (5 mL) and assayed by GC to contain 545 mg of CPA (91% assay yield).

A mixture of cyclopropaneacetylene carboxylic acid (1.00; 9.08mmol) and cuprous chloride (45 mg; 0.45 mmol) in DMF (10 mL) was heated to about 100° C. (bath temperature) in a distillation setup. Pure product (boiling point 52° C.) was collected (545 mg; 91%).

What is claimed is:

1. A process for the preparation of cyclopropaneacetylene comprising the steps of:
   (a) alkylating propiolic acid with a 1,3-disubstituted propane in a first base and an aprotic solvent to produce a reaction mixture containing a 6-substituted 2-hexynoic acid;
   (b) intramolecular cycloalkylation of the 6-substituted 2-hexynoic acid by addition of a second base to produce a reaction mixture containing cyclopropaneacetylene carboxylic acid; and
   (c) decarboxylating the cyclopropaneacetylene carboxylic acid with a copper catalyst in a polar aprotic solvent to give cyclopropaneacetylene.

2. The process of claim 1, wherein the aprotic solvent is selected from the group consisting of tetrahydrofuran, 2,5-dimethyltetrahydrofuran, 1,4-dioxane, 1,3-dioxolane, methyl-tert-butyl ether, diethoxymethane, dimethoxyethane, cyclohexane, pentane, hexane, toluene, hexamethyl phosphoric triamide, dimethylpropyleneurea, and mixtures of thereof.

3. The process of claim 2, wherein the aprotic solvent is a mixture of hexamethyl phosphoric triamide and tetrahydrofuran.

4. The process of claim 3, wherein the first base is present in amounts between about 1.0 equivalent to about 3.0 equivalents relative to the amount of propiolic acid.

5. The process of claim 4, wherein the first base is present in amounts between about 2.0 equivalents to about 2.5 equivalents relative to the amount of propiolic acid.

6. The process of claim 5, wherein the first base is selected from the group consisting of sodium hydride, lithium hydride, potassium hydride, alkyl lithium, and alkyl potassium.

7. The process of claim 6, wherein the first base is n-butyl lithium.

8. The process of claim 7, wherein a reaction of the mixture in step (a) of claim 1 occurs at a temperature range of between about 0° C. and about −100° C. for about 30 minutes to about two hours.

9. The process of claim 8, wherein the 1,3-disubstituted propane is a compound having a chemical formula X—(CH$_2$)$_3$—X wherein X is the same substituent or mixtures of different substituent, which is selected from the group consisting of Cl, Br, I, perfluoroalkyl sulfonates, alkyl sulfonates, and aryl sulfonates.

10. The process of claim 9, wherein the 1,3-disubstituted propane is 1-bromo-3-chloropropane.

11. The process of claim 10, wherein the second base is a non-nucleophilic base.

12. The process of claim 11, wherein the non-nucleophilic base is selected from the group consisting of lithium diisopropylamide, lithium bis(trimethylsilyl)amide, sodium bis(trimethylsilyl)amide, potassium bis(trimethylsilyl) amide, potassium tert-butoxide, sodium hydride, lithium hydride, and potassium hydride.

13. The process of claim 12, wherein the non-nucleophilic base is lithium diusopropylamide.

14. The process of claim 13, wherein the first and the second base are the same.

15. The process of claim 14, wherein a reaction of the step (b) of claim 1 occurs at a temperature between about −10° C. and about −20° C. for about an hour to about two hours.

16. The process of claim 15 further comprises the steps of isolating the cyclopropaneacetylene carboxylic acid in step (b) of claim 1 by acidifying the mixture and washing the mixture with organic solvent.

17. The process of claim 16, wherein the polar aprotic solvent is selected from the group consisting of dimethyl formamide, dimethylacetamide, acetonitrile, N-methyl-pyrrolidinone, and mixtures thereof.

18. The process of claim 17, wherein the polar aprotic solvent is dimethyl formamide.

19. The process of claim 18, wherein the copper catalyst is Cu, CuX, or CuX$_2$, and wherein X is selected from the group consisting of Cl, Br, I, SO$_4$, CN, ClO$_4$, NO$_3$, acetylacetonate, CH$_3$CO$_2$, and CF$_3$SO$_2$.

20. The process of claim 19, wherein the copper catalyst is CuCl.

21. The process of claim 20, wherein the decarboxylation of cyclopropaneacetylene carboxylic acid in step (c) of claim 1 occurs at temperature between about 50° C. and about 100° C. for about an hour to about two hours.

* * * * *